United States Patent
Avrahami

(10) Patent No.: US 6,615,079 B1
(45) Date of Patent: Sep. 2, 2003

(54) TRANSDERMAL DRUG DELIVERY AND ANALYTE EXTRACTION

(75) Inventor: Zohar Avrahami, Rehovot (IL)

(73) Assignee: Elecsys Ltd., Rishon le Zion (IL)

( * ) Notice: Subject to any disclaimer, the term of this patent is extended or adjusted under 35 U.S.C. 154(b) by 0 days.

(21) Appl. No.: 09/635,892

(22) Filed: Aug. 10, 2000

Related U.S. Application Data

(62) Division of application No. 09/189,170, filed on Nov. 9, 1998, now Pat. No. 6,148,232.

(51) Int. Cl.$^7$ ............................................... A61N 1/30
(52) U.S. Cl. ................................................... 604/20
(58) Field of Search .................. 604/19–21; 607/2, 607/3, 152; 600/391, 372

(56) References Cited

U.S. PATENT DOCUMENTS

| | | |
|---|---|---|
| 3,964,482 A | 6/1976 | Grestel |
| 4,775,361 A | 10/1988 | Jacques et al. |
| 4,943,290 A | 7/1990 | Rexroth et al. |
| 5,019,034 A | 5/1991 | Weaver et al. |
| 5,135,478 A | 8/1992 | Sibalis |
| 5,165,418 A | 11/1992 | Tankovich |
| 5,196,709 A | 3/1993 | Berndt et al. |
| 5,232,441 A | 8/1993 | Stephen et al. |
| 5,246,867 A | 9/1993 | Lakowicz et al. |
| 5,281,825 A | 1/1994 | Berndt et al. |
| 5,328,452 A | 7/1994 | Sibalis |
| 5,380,272 A | 1/1995 | Gross |
| 5,409,835 A | 4/1995 | Lakowicz et al. |
| 5,421,817 A | 6/1995 | Liss et al. |
| 5,423,803 A | 6/1995 | Tankovich et al. |
| 5,439,440 A | 8/1995 | Hoffman |
| 5,458,140 A | 10/1995 | Eppstein et al. |
| 5,485,530 A | 1/1996 | Lakowicz et al. |
| 5,500,437 A | 3/1996 | Saitoh et al. |
| 5,571,149 A | 11/1996 | Liss et al. |
| 5,582,168 A | 12/1996 | Samuels et al. |
| 5,624,847 A | 4/1997 | Lakowicz et al. |
| 5,628,310 A | 5/1997 | Rao et al. |
| 5,631,169 A | 5/1997 | Lakowicz et al. |
| 5,648,269 A | 7/1997 | Lakowicz et al. |
| 5,651,765 A * | 7/1997 | Haworth et al. .............. 604/20 |

(List continued on next page.)

FOREIGN PATENT DOCUMENTS

| | | |
|---|---|---|
| EP | 0547482 | 6/1993 |
| WO | WO9310854 | 6/1993 |
| WO | WO9416765 | 8/1994 |
| WO | WO9427671 | 12/1994 |
| WO | WO 00/69515 | 11/2000 |
| WO | WO 00/74767 | 12/2000 |

OTHER PUBLICATIONS

Henry et al., "Micromachined needles for the transdermal delivery of drug", IEEE 11$^{th}$ Annual International Workshop on Micro–Electro–Mechanical Systems, 1998, pp. 494–498.

Chizmadzhev, et al., "Electrical properties of skin at moderate voltages", Biophysics Journal, Feb. 1998, 74(2), pp. 843–856.

"Instructions Manual for the Force 2 Electrosurgical Generator", Valleylab/TycoHealthcare Group LP, Boulder, Colorado, 1999.

*Primary Examiner*—Sharon Kennedy
(74) *Attorney, Agent, or Firm*—Abelman, Frayne & Schwab

(57) ABSTRACT

A device for ablating the stratum corneum epidermidis of a subject, including a plurality of electrodes, which are applied to the subject's skin at respective points. A power source applies electrical energy between two or more of the plurality of electrodes, in order to cause ablation of the stratum corneum primarily in an area intermediate the respective points.

32 Claims, 6 Drawing Sheets

U.S. PATENT DOCUMENTS

| | | | |
|---|---|---|---|
| 5,660,991 A | | 8/1997 | Lakowicz et al. |
| 5,674,267 A | | 10/1997 | Mir et al. |
| 5,688,232 A | | 11/1997 | Flower et al. |
| 5,697,896 A | | 12/1997 | McNichols et al. |
| 5,720,772 A | * | 2/1998 | Eckhouse .................... 607/88 |
| 5,722,397 A | | 3/1998 | Eppstein |
| 5,759,767 A | | 6/1998 | Lakowicz et al. |
| 5,792,049 A | | 8/1998 | Eppstein et al. |
| 5,860,421 A | | 1/1999 | Epstein et al. |
| 5,871,469 A | * | 2/1999 | Eggers et al. ............... 604/114 |
| 5,885,211 A | | 3/1999 | Eppstein et al. |
| 5,902,272 A | * | 5/1999 | Eggers et al. ............... 604/114 |
| 5,911,223 A | | 6/1999 | Weaver et al. |
| 5,924,981 A | | 7/1999 | Rothfritz et al. |
| 5,938,657 A | * | 8/1999 | Assa et al. ..................... 606/9 |
| 5,964,726 A | | 10/1999 | Korenstein et al. |
| 5,983,130 A | | 11/1999 | Phipps et al. |
| 5,983,131 A | | 11/1999 | Weaver et al. |
| 6,002,482 A | | 12/1999 | Rothfritz et al. |
| 6,009,344 A | | 12/1999 | Flower |
| 6,022,316 A | * | 2/2000 | Eppstein et al. ............ 600/309 |
| 6,024,733 A | | 2/2000 | Eggers et al. |
| 6,030,399 A | | 2/2000 | Ignotz et al. |
| 6,041,253 A | | 3/2000 | Kost et al. |
| 6,045,502 A | | 4/2000 | Epstein et al. |
| 6,050,988 A | | 4/2000 | Zuch |
| 6,055,451 A | | 4/2000 | Bambot et al. |
| 6,066,134 A | * | 5/2000 | Eggers et al. ................. 606/32 |
| 6,076,012 A | * | 6/2000 | Swanson et al. .............. 604/21 |
| 6,083,196 A | | 6/2000 | Trautman et al. |
| 6,088,606 A | | 7/2000 | Ignotz et al. |
| 6,090,106 A | | 7/2000 | Goble et al. |
| 6,104,952 A | * | 8/2000 | Tu et al. ....................... 604/20 |
| 6,117,109 A | * | 9/2000 | Eggers et al. ............... 604/114 |
| 6,142,939 A | | 11/2000 | Eppstein et al. |
| 6,142,992 A | * | 11/2000 | Cheng et al. ................. 606/34 |
| 6,148,232 A | | 11/2000 | Avrahami |
| 6,159,194 A | | 12/2000 | Eggers et al. |
| 6,173,202 B1 | | 1/2001 | Eppstein et al. |
| 6,183,434 B1 | | 2/2001 | Eppstein |
| 6,192,734 B1 | | 2/2001 | Rothfritz et al. |
| 6,210,402 B1 | * | 4/2001 | Olsen et al. .................. 606/32 |
| 6,228,078 B1 | * | 5/2001 | Eggers et al. ................. 606/32 |
| 6,235,020 B1 | * | 5/2001 | Cheng et al. ................. 606/34 |
| 6,238,391 B1 | * | 5/2001 | Olsen et al. .................. 606/41 |

* cited by examiner

TRANSDERMAL DRUG DELIVERY AND ANALYTE EXTRACTION

This appln. is a divisional of Ser. No. 09/189,170 filed Nov. 9, 1998 now U.S. Pat. No. 6,148,232.

FIELD OF THE INVENTION

The present invention relates generally to methods and devices for drug delivery and analyte extraction, and specifically to medical methods and devices for puncturing the outer layer of living skin and to methods and devices for transdermal drug delivery and analyte extraction.

BACKGROUND OF THE INVENTION

A number of different methods have been developed to perform transdermal drug delivery and/or analyte extraction, including passive diffusion of a drug or analyte between a skin patch and skin, as well as active processes such as iontophoresis, sonophoresis, electroporation, and chemically enhanced diffusion. These methods are primarily used for generating transdermal movement of small molecules, but generally do not enhance the motion of large molecules through the 10–50 micron thick outermost layer of the skin, the stratum corneum epidermidis.

In an article, "Micromachined needles for the transdermal delivery of drugs," IEEE 11th Annual International Workshop on Micro-Electro-Mechanical Systems (1998), pp. 494–498, which is incorporated herein by reference, Henry et al. discuss a method of mechanically puncturing the skin with microneedles in order to increase the permeability of skin to a test drug. In the article, microfabrication techniques are described to etch an array of needles in silicon, and experiments performed on cadaver skin with the needle array demonstrated an increase in permeability subsequent to puncture of the skin. The needles are created with a predetermined length, and penetrate to the same depth from the skin surface, regardless of the local thickness of the stratum-corneum. It is known that if the needles are longer than the local thickness, then the underlying epidermal tissue may be injured, while if the needles are too short, channel formation through the stratum corneum may be incomplete.

U.S. Pat. Nos. 4,775,361, 5,165,418, and 5,423,803, and PCT Publication WO 97/07734, the disclosures of which are incorporated herein by reference, describe methods of using laser pulses to locally heat the stratum corneum to about 120° C., thereby causing local ablation, in order to cause a single hole to develop in the stratum corneum through which large molecules may pass. Whereas some selectivity of ablation depth can be attained by varying the wavelength of the laser pulse, no feedback mechanism is disclosed whereby the laser pulses are terminated upon generation of the necessary damage to the stratum corneum.

PCT Publication WO 97/07734 also discloses thermal ablation of the stratum corneum using an electrically resistive element in contact with the stratum corneum, such that a high current through the element causes a general heating of tissue in its vicinity, most particularly the stratum corneum. As above, no means are disclosed to terminate current flow upon sufficient disruption of the stratum corneum. Additionally, thermal characteristics of skin vary highly across different areas of an individual's skin, as well as among a group of subjects, making optimal thermal dosages, which produce the desired ablation without causing pain, very difficult to determine. Lastly, increasing transdermal molecular flow by increasing the permeability of the stratum corneum, whether using microneedles, laser energy, or resistive heating of tissue, is inherently a two step process: (a) position apparatus to generate holes, and (b) apply a patch to the skin, through which the molecules will flow.

Electroporation is also well known in the art as a method to increase pore size by application of an electric field. This process is described in an article by Chizmadzhev et al., entitled "Electrical properties of skin at moderate voltages," Biophysics Journal, February, 1998, 74(2), pp. 843–856, which is incorporated herein by reference. Electroporation is disclosed as a means for transiently decreasing the electrical resistance of the stratum corneum and increasing the transdermal flux of small molecules by applying an electric field to increase the size of existing pores. Electroporation generally does not produce pores of sufficient diameter to pass large molecules therethrough. Additionally, optimal voltage profiles are difficult to determine because of naturally occurring variations as described hereinabove, as well as the lack of an accurate feedback mechanism to indicate achievement of the desired pore enlargement. If excessive voltage is applied, an irreversible breakdown occurs, resulting in damage to the skin and possible sensations of pain.

U.S. Pat. No. 5,019,034 to Weaver et al., whose disclosure is incorporated herein by reference, describes apparatus for applying high voltage, short duration electrical pulses on the skin to produce electroporation, and states that ". . . reversible electrical breakdown . . . along with an enhanced tissue permeability, is the characteristic effect of electroporation."

SUMMARY OF THE INVENTION

It is an object of some aspects of the present invention to provide improved apparatus and methods for transdermal delivery of an active substance.

It is a further object of some aspects of the present invention to provide improved apparatus and methods for transdermal analyte extraction.

It is yet a further object of some aspects of the present invention to provide improved apparatus and methods for creating narrow channels through the stratum corneum of living skin by puncturing.

It is still a further object of some aspects of the present invention to provide improved apparatus and methods for reducing sensation and minimizing damage to skin underlying the stratum corneum during channel creation.

It is an additional object of some aspects of the present invention to provide improved apparatus and methods for controlling the timing of channel creation.

It is yet an additional object of some aspects of the present invention to provide improved apparatus and methods for regulating channel creation responsive to properties of the skin.

It is another object of some aspects of the present invention to provide improved apparatus and methods for puncturing the skin and/or transdermally delivering an active substance and/or transdermally extracting an analyte, using a miniature, self-contained device.

It is yet another object of some aspects of the present invention to provide improved apparatus and methods for transdermally delivering an active substance using a standard medical skin patch.

In preferred embodiments of the present invention, a device for enhancing transdermal movement of a substance comprises: (a) a skin patch, with at least two electrodes in contact with the skin of a subject; and (b) a control unit, coupled to the patch, which causes a current to pass between the electrodes through the stratum corneum epidermidis, in order to generate at least one micro-channel in the stratum corneum to enable or augment transdermal movement of the substance. Preferably, the control unit comprises switching circuitry to control the magnitude and/or duration of the electric field at the electrode.

The term "micro-channel" as used in the context of the present patent application and in the claims refers to a pathway generally extending from the surface of the skin through all or a significant part of the stratum corneum, through which pathway molecules can diffuse. Preferably, micro-channels allow the diffusion therethrough of large molecules at a greater rate than the same molecules would diffuse through pores generated by electroporation. It is believed that such micro-channels are formed due to local power dissipation leading to ablation of the stratum corneum when an electric field of sufficient magnitude is applied to a small area of the skin, in contact with the electrodes, for a certain period of time. Unlike methods of electrically-promoted drug delivery known in the art, such as iontophoresis and electroporation, the present invention enables relatively large channels to be formed, through which even large molecules of the active substance can pass rapidly, without the necessity of ionizing or polarizing the molecules.

The current flow between the electrodes can be described as having two components: (a) a perpendicular component, which is generally perpendicular to the skin surface (and, if the associated electric field is sufficiently large, may cause current to go through the stratum corneum into the underlying epidermal tissue and dermis); and (b) a lateral component, generally parallel to the skin surface, which remains generally within the stratum corneum. Substantially all of the current generated at one electrode ultimately emerges from the skin and is taken up by an adjacent electrode.

In preferred embodiments of the present invention, methods and/or apparatus are employed to increase the relative value of the lateral component with respect to the perpendicular component. In general, the stratum corneum epidermidis (the superficial layer of the epidermis) demonstrates a significantly higher resistance to the passage of molecules therethrough than does the underlying epidermal tissue. It is therefore an object of these preferred embodiments of the present invention to form micro-channels in the stratum corneum by ablating the stratum corneum in order to increase conductance of the substance therethrough, and to generally not directly affect or damage epidermal tissue underlying the stratum corneum or in the innervated dermis. Additionally, limiting current flow substantially to the non-innervated stratum corneum is expected to decrease or eliminate the subject's sensations, discomfort, or pain responsive to use of the present invention, particularly as compared with other procedures known in the art.

A voltage applied between two electrodes on the skin generates an electric field that is to a large extent confined to the volume in a vicinity of the electrodes. Thus, electrodes which are widely spaced produce a field—and current flow responsive thereto—which extends relatively deep into the skin. Conversely, electrodes which are closely spaced do not generate significant current flow at deeper layers. Therefore, in some preferred embodiments of the present invention, the electrodes of the device are separated by distances smaller than about 100 microns (but for some applications by distances of up to approximately 500 microns), in order to generate a current flow which is largely confined to a thin layer, comprising most or all of the stratum corneum. This effectively results in a desired larger value of the ratio of the lateral component to the perpendicular component, as described hereinabove.

In some of these preferred embodiments of the present invention, a high-frequency AC current with an optional DC current added thereto is applied between the closely-spaced electrodes in order to generate lateral capacitive currents in the stratum corneum and to cause breakdown and micro-channel formation in the stratum corneum.

In some preferred embodiments of the present invention, the patch comprises an array of electrodes, preferably closely-spaced electrodes, which act together to produce a high micro-channel density in an area of the skin under the patch. Preferably, the control unit and/or associated circuitry sequentially or simultaneously evaluates the current flow through each electrode, or a subset of the electrodes, in order to determine when one or more micro-channels have formed responsive to the applied field. Responsive thereto, the control unit discontinues application of the field. Since the formation of a micro-channel is typically marked by a local drop in electrical resistance of the skin, the control unit may, for example, reduce the voltage or current applied at any electrode wherein the current has exceeded a threshold. By reducing current flow upon or shortly after micro-channel formation, the likelihood of skin burns or pain sensations is minimized.

In some preferred embodiments of the present invention, a relatively high voltage is applied to the electrodes initially, so as to induce formation of micro-channels through the skin. A property of the current flow is detected, and the current is reduced or terminated when the property reaches a predetermined threshold. Preferably, the detected property of the current flow is secondary to changes in a conduction property of the skin, responsive to formation of one or more micro-channels through the stratum corneum.

Alternatively or additionally, a time-varying voltage $V(t)$, characterized, for example, by the formula $V(t)=V_0+kt^n$, is applied between a first electrode and a second electrode in the skin patch until a shut-off signal is generated. (Constants k and n are nonnegative.) Other forms of $V(t)$ may include a sinusoid, an exponential term, or a series of pulses. A current $I(t)$, flowing responsive to the applied field, is measured by the control unit, as described hereinabove. Calculations of the values of $\int I(t)dt$, $dI/dt$ and/or $d^2I/dt^2$ are frequently performed. Comparisons of $I$ and/or $\int I(t)dt$ and/or $dI/dt$ and/or $d^2I/dt^2$ with respective threshold values are used as indicators of micro-channel formation and/or to determine when to generate the shutoff signal for the electrodes.

Further alternatively or additionally, in embodiments in which $V(t)$ is sinusoidal, the control unit preferably calculates changes in a phase shift between $V(t)$ and $I(t)$ during application of the electric field, and controls the field responsive to these changes. It is believed that cells in the stratum corneum demonstrate capacitance, which causes the phase shift, and that ablation of the stratum corneum decreases the capacitance and is evidenced by a decrease in the phase shift.

Still further alternatively or additionally, the total charge which is passed through the skin is limited by a capacitor, inductor, or other energy-storage device. An appropriate choice of values for these components sets an absolute maximum quantity of charge which can pass through the skin, and thus limits any damage that can be caused thereby.

In some preferred embodiments of the present invention, one or more of the electrodes comprise or are coupled to an electrically conductive dissolving element, where the dissolving rate is generally proportional to the current passing through the electrode. When a sufficient quantity of charge has passed through the dissolving element, the electrode ceases to conduct electricity. Thus, a maximum total charge, $Q_{total}$, is associated with an electrode, such that current flows through the element for only as long as $q(t) \equiv \int I(t) dt < Q_{total}$. This serves as a safety feature, reducing the possibility of skin burns secondary to applied electric fields. Alternatively or additionally, the dissolving element is constructed so that it becomes non-conductive after a quantity of charge has passed therethrough which is sufficient to ablate the stratum corneum.

In some further preferred embodiments of the present invention, the electrodes are "printed" directly on the skin, preferably by stamping or by employing a transfer patch of a conductive substance (such as, for example, a conductive ink containing silver grains). In applications of such embodiments of the present invention for transdermal drug delivery, the conductive substance preferably comprises a matrix holding the drug to be administered to a subject.

Preferably, the printed electrodes demonstrate a substantially complete loss of conductance therethrough upon ablation of the stratum corneum responsive to the applied electric field. Further preferably, each printed electrode comprises a material which is conductive only when current flowing therethrough remains below a threshold value. If the current exceeds the threshold, then thermal fusion of the material causes it to become largely nonconductive, i.e. the material acts as a fuse. Still further preferably, current continues to flow through the other electrodes until they reach the threshold current, at a time which is generally associated with the time required for ablation of the stratum corneum, as described hereinabove. In some of these embodiments, the control unit may be made substantially simpler than as described regarding other embodiments, and generally does not need other circuitry in order to determine whether to generate a shut-off signal.

In still further preferred embodiments of the present invention, two electrodes on the patch form a concentric electrode pair, in which an inner electrode generates a current which passes through the stratum corneum to an outer electrode surrounding the inner electrode. The distance between the inner and outer electrodes is preferably between about 50 and about 200 microns, in order to maintain the ratio of the lateral to the perpendicular component of the current at a high value, as described hereinabove.

In some preferred embodiments of the present invention, a conductance-enhancing substance, preferably comprising a conductive cream or ink, is applied to the skin in order to increase the ratio of the lateral to the perpendicular component of current flow. Alternatively or additionally, the conductance-enhancing substance comprises a composition with a high diffusion coefficient, which diffuses into the lipid layers of the stratum corneum and further augments the selective power dissipation therein, in order to ablate the stratum corneum with substantially little damage to the underlying tissue. In some applications, the substance has an electrical charge associated therewith, such that when a small lateral field is applied, lateral diffusion of the substance within the stratum corneum is enhanced (i.e., iontophoresis of the substance).

In some of these preferred embodiments which utilize a conductance-enhancing substance, the substance further comprises an active substance, for example, a pharmaceutical product, dissolved or mixed therein. Since breakdown of the stratum corneum is often associated with removal of the enhanced conductivity path afforded by the conductance-enhancing substance, it is preferable in many of these embodiments to use a substantially constant voltage source to generate current at the electrodes. Removal of the enhanced conductivity path will result in a desired reduced power dissipation in the stratum corneum ($P=V^2/R$), since the voltage remains constant while resistance increases.

In other preferred embodiments of the present invention, ablation of the stratum corneum is accomplished using a current-limited source to power the electrodes. It is believed that the stratum corneum generally displays high electrical resistance, while epidermal tissue underlying the stratum corneum has significantly lower electrical resistance. Ablation of the stratum corneum (i.e., removal of the high-resistance tissue) is therefore associated with a net decrease of electrical resistance between the electrodes, and the power dissipated in the epidermis following electrical breakdown will decrease, typically proportional to the change in resistance ($P=I^2R$).

Monitoring changes in voltage, current, and/or phase for each electrode in the control unit may require, in certain implementations, a significant amount of circuitry. Therefore, in some preferred embodiments of the present invention, the control unit comprises one or more clusters of electrodes, in which monitoring and control are performed for each cluster rather than for the individual electrodes therein. The cluster is preferably over a relatively small area of skin, for example, from about 1 mm$^2$ to about 100 mm$^2$ in which properties of the skin are assumed to be substantially constant.

In some preferred embodiments of the present invention, the device is a stand-alone device, which enables transdermal delivery of an active substance or enhances transdermal motion of an analyte. Alternatively, the device creates micro-channels as described hereinabove and is then removed from the skin, in order to enhance the transdermal delivery of a substance into or out of a commercially-available skin patch subsequently placed on the skin. In other preferred embodiments of the present invention, the device is an add-on to commercially available transdermal drug delivery/analyte extraction devices, and serves primarily to create the micro-channels in the stratum corneum, and optionally to act as a vehicle through which the substance may pass.

There is therefore provided, in accordance with a preferred embodiment of the present invention, a device for ablating the stratum corneum epidermidis of a subject, including:

a plurality of electrodes, which are applied to the subject's skin at respective points; and a power source, which applies electrical energy between two or more of the plurality of electrodes, to cause ablation of the stratum corneum primarily in an area intermediate the respective points.

Preferably, skin layers beneath the stratum corneum are substantially not ablated. In a preferred embodiment of the present invention, the ablation of the stratum corneum causes a puncturing thereof.

Preferably, the device ablates the area of the stratum corneum in order to allow a substance to pass therethrough. Further preferably, the substance includes a drug that is delivered through the skin. Alternatively, the substance includes an analyte that is extracted through the skin.

Preferably, the power source generates an electric field which causes a current to flow through the stratum corneum, and the device reduces power dissipated in the stratum corneum responsive to variation of a characteristic of the current. Further preferably, the characteristic is drawn from a list consisting of: the magnitude of the current; a time-integration of the current; a first time-derivative of the current; and a second time-derivative of the current.

Alternatively or additionally, current through one of the plurality of electrodes is reduced substantially independently of the current through another one of the plurality of electrodes.

Further alternatively or additionally, at least one of the plurality of electrodes is coupled to receive the current through a limited-conduction unit, which unit allows current below a threshold value to flow therethrough substantially unimpeded, and becomes substantially non-conductive if the current flowing therethrough exceeds a limited-conduction threshold value.

Preferably, at least one of the plurality of electrodes is coupled to an electrically-conductive dissolving element characterized by a dissolving rate generally proportional to the current passing therethrough, which becomes substantially nonconductive responsive to a function of the current. In a preferred embodiment, the function includes a time-integral of the current having passed through the dissolving element.

Preferably, the dissolving element includes:

an electrolyte solution within the element; and a first node and a common node immersed in the electrolyte solution,
  wherein current flows from the first node to the common node through the electrolyte solution, the current flow causing the common node to be consumed at a rate generally proportional to the current passing therethrough, such that the dissolving element becomes substantially nonconductive when the total charge having passed through the common node exceeds a common node threshold value.

Further preferably, the dissolving element also includes a second node, immersed in the electrolyte solution, wherein the power source generates alternating current; and wherein the device further includes:

a first diode, coupled in series between the power source and the first node, which conducts current from the power source to the first node when the alternating current is in a positive phase thereof; and a second diode, coupled in series between the power source and the second node, which conducts current from the second node to the power source when the alternating current is in a negative phase thereof, such that the dissolving element becomes substantially nonconductive when the total charge having passed through the common node exceeds a common node threshold value.

Alternatively, the dissolving element includes:

an electrolyte solution within the element;

a large-area anode immersed in the electrolyte solution; and a plurality of cathodes, immersed in the electrolyte solution, each of the cathodes being coupled to a respective one of the plurality of electrodes,
  wherein current flows from the large-area anode to the plurality of cathodes through the electrolyte solution, the current flow causing at least one of the cathodes to be consumed at a rate generally proportional to the current passing therethrough, and wherein the at least one cathode becomes substantially nonconductive responsive to a function of the current having passed therethrough.

Preferably, the current through at least one of the plurality of electrodes is reduced responsive to the variation of the characteristic of the current through another one of the plurality of electrodes.

In a preferred embodiment, the device also includes a voltage sensing unit coupled to measure a voltage drop across two of the plurality of electrodes, and current from the power source is reduced responsive to the measurement made by the sensing unit. Preferably, the power source includes a current source, and current from the current source is reduced responsive to a measurement made by the sensing unit which indicates that the electrical potential between the two electrodes is below a voltage-threshold value.

Alternatively or additionally, the device includes a resistive element coupled to one of the two electrodes and to the power source, and the voltage sensing unit is further coupled to measure a voltage drop across the resistive element in order to determine a current passing therethrough. The power source includes an alternating current source, such that the measurements of the voltage drop across the two electrodes and the current through the resistive element determine a phase shift. The current from the alternating current source is reduced responsive to the phase shift being below a threshold value.

In a preferred embodiment, the device includes:

a resistive element coupled to one of the plurality of electrodes and to the power source; and a voltage sensing unit coupled to measure a voltage drop across the resistive element in order to determine a current passing therethrough.

In this preferred embodiment, the power source includes a voltage source, and the voltage is reduced responsive to a measurement made by the sensing unit which indicates that the current through the resistive element is above a current-threshold value.

In another preferred embodiment, at least one of the plurality of electrodes is printed directly on the skin and becomes substantially electrically nonconductive responsive to the value of the current passing therethrough being greater than a threshold value.

In yet another preferred embodiment, the device includes:

a capacitor, coupled to two of the plurality of electrodes; and a switch, coupled to the power source and the capacitor, such that the switch, in a closed phase thereof, allows current to flow from the power source to the capacitor and to the two electrodes, and such that the switch, in an open phase thereof, substantially terminates current flow from the power source to the capacitor and to the two electrodes.

In this embodiment, the power source charges the capacitor during the closed phase, and the capacitor discharges current through the electrodes during the open phase.

Preferably, the distance between two of the plurality of electrodes is less than about 0.3 mm. Further preferably, the distance between two of the plurality of electrodes is between about 0.01 mm and about 0.1 mm.

Preferably, the plurality of electrodes include:

a common electrode, which has a plurality of perforations therethrough; and a plurality of positive electrodes, each positive electrode passing through a respective perforation of the common electrode, such that current from the power source flows from each positive electrode through the skin to the common electrode.

In a preferred embodiment, the power source generates alternating current, a frequency thereof being above about 100 Hz. Preferably, the frequency is between about 1 kHz and about 300 kHz. Alternatively or additionally, the power source modulates a frequency of the alternating current between a first frequency value and a second frequency value.

There is further provided, in accordance with a preferred embodiment of the present invention, a device for passing electrical current through the skin of a subject, including:

a power source, which generates the current;

a plurality of electrodes, which are applied to the skin at respective points; and an electrically conductive dissolving element coupled to at least one of the electrodes, the element being characterized by a dissolving rate generally proportional to the current passing therethrough, and becoming substantially nonconductive responsive to a function of the current passing therethrough.

There is also provided, in accordance with a preferred embodiment of the present invention, a method for ablating the stratum corneum epidermidis of a subject, including:

placing a plurality of electrodes against the subject's skin at respective points; and applying electrical energy between two or more of the plurality of electrodes, in order to cause ablation of the stratum corneum primarily in an area intermediate the respective points.

Preferably, skin layers beneath the stratum corneum are substantially not ablated. In a preferred embodiment, applying the electrical energy includes puncturing the skin.

Preferably, applying the energy includes ablating the area of the stratum corneum in order to allow a substance to pass through the area. Further preferably, the method includes delivering a drug or extracting an analyte through the area.

Preferably, applying electrical energy includes:

causing a current to flow through the points on the skin; and substantially reducing the current flow through the skin responsive to variation of a characteristic of the current.

In a preferred embodiment, the characteristic is drawn from a list consisting of: a magnitude of the current; a time-integration of the current; a first time-derivative of the current; and a second time-derivative of the current.

In another preferred embodiment, causing the current to flow includes passing current to the one or more points on the skin through one or more respective limited-conduction units, wherein the units allow current below a threshold value to flow therethrough substantially unimpeded, and wherein the units become substantially nonconductive if the current flowing therethrough exceeds a limited-conduction threshold value.

In another preferred embodiment, causing the current to flow includes -passing current to the one or more points on the skin through one or more respective electrically conductive dissolving elements, each element characterized by a dissolving rate generally proportional to the current passing therethrough, and each element becoming substantially nonconductive when the total charge having passed therethrough exceeds a dissolving element threshold value.

In yet another preferred embodiment, reducing the current flow includes reducing the current at one of the respective points substantially independently of the current at another one of the respective points.

In still another preferred embodiment, reducing current flow includes:

monitoring the current flow through one of the plurality of electrodes; and reducing the current flow through another one of the plurality of electrodes responsive thereto.

Preferably, placing the plurality of electrodes includes placing two of the plurality of electrodes at a separation therebetween that is less than about 0.3 mm. Further preferably, placing the plurality of electrodes includes placing the two of the plurality of electrodes at a separation between about 0.01 mm and about 0.1 mm.

In a preferred embodiment, placing the plurality of electrodes includes:

applying a conduction-enhancing material to an area on the surface of the subject's skin in order to enhance current flow through the skin; and placing the electrodes on the material, wherein the electrical resistance of the conduction-enhancing material increases responsive to a function of the current flow therethrough.

Preferably, placing the plurality of electrodes includes:

placing on the skin a common electrode which has a plurality of perforations therethrough; and placing on the skin a plurality of positive electrodes, each positive electrode passing through a respective perforation in the common electrode, such that current from the power source flows from each positive electrode through the skin to the common electrode.

Further preferably, the method includes positioning in a vicinity of the electrodes a medical patch containing the substance, such that ablation of the stratum corneum increases a transport rate of the substance from the patch into the skin.

In a preferred embodiment, applying electrical energy includes generating alternating current, a frequency thereof being above about 100 Hz. Preferably, the frequency is between about 1 kHz and about 300 kHz. Alternatively or additionally, applying electrical energy includes modulating a frequency of the alternating current between a first frequency value and a second frequency value.

There is additionally provided, in accordance with a preferred embodiment of the present invention, a method for passing electrical current through the skin of a subject, including:

placing a plurality of electrodes against the skin at respective points;

applying the current through the electrodes; and coupling to at least one of the electrodes an electrically conductive dissolving element, the element being characterized by having a dissolving rate generally proportional to the current passing therethrough, and by becoming substantially nonconductive responsive to a function of the current passing therethrough.

The present invention will be more fully understood from the following detailed description of the preferred embodiments thereof, taken together with the drawings in which:

DETAILED DESCRIPTION OF PREFERRED EMBODIMENTS

Figure 1A:
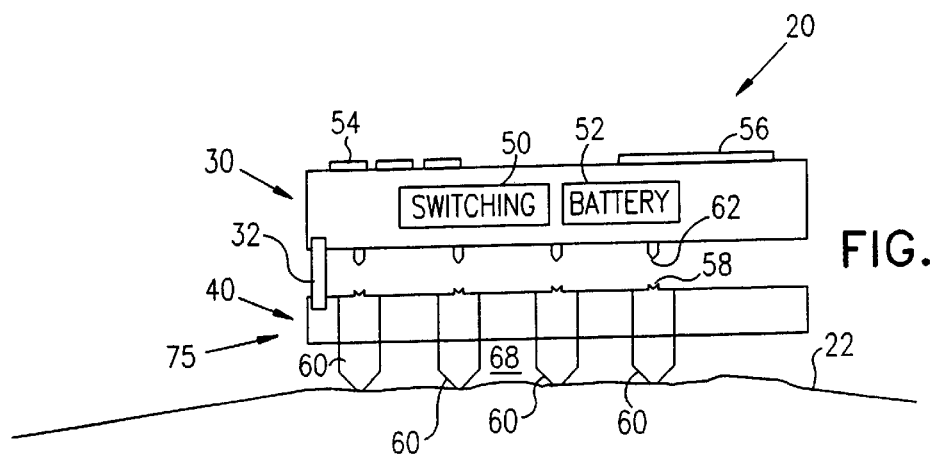
FIG. 1A is a schematic, partly sectional illustration of a device for transdermal transport of a substance, in accordance with a preferred embodiment of the present invention.

FIG. 1A is a schematic, partly sectional illustration of a skin puncturing device 20 for transdermal delivery of an active substance and/or transdermal extraction of an analyte, in accordance with a preferred embodiment of the present invention. Device 20 comprises a control unit 30 attached to a skin patch 40, which is preferably fixed to a suitable area of a subject's skin 22. Device 20 preferably administers an active substance through the normally substantially-impermeable stratum corneum layer of the skin by passing a controlled electric current therethrough, thereby ablating the stratum corneum and generating micro-channels through which the substance can pass. Alternatively or additionally, device 20 is used to generate micro-channels in the stratum corneum in order to allow passage of molecules to patch 40 from the underlying tissue, generally for diagnostic purposes.

When device 20 drives current through the stratum corneum, this tissue is heated resistively, so that when a sufficient quantity of energy has passed therethrough in a short time period, the tissue is ablated by the total energy dissipated therein. This ablation creates the desired micro-channels, i.e. physical gaps in the tissue. It has been found that application of a current to a small area of the skin leads to formation of such micro-channels, through which even large molecules can pass relatively freely, without the necessity of ionizing or polarizing the molecules, and without causing pain or substantial trauma to the dermis and epidermal tissue underlying the stratum corneum.

Control unit 30 preferably comprises a switching unit 50, a battery 52 (such as a lithium coin cell battery), and an optional user-interface comprising buttons 54 and a sensible signal generator 56, which may comprise a display and/or a buzzer. In a simplest embodiment, buttons 54 initialize and terminate analyte extraction or delivery of the active substance, although buttons 54 preferably also programmably control extraction or dosage rate and duration.

Patch 40 comprises two or more electrodes 60, preferably an array 75 of electrodes, which pass current into and out of the skin. In applications of device 20 for transdermal drug delivery, when a micro-channel has formed responsive to current flow between the electrodes, the active substance stored in patch 40 flows therethrough. In the patch, the active substance is preferably stored in or applied to inter-electrode regions 68 and flows directly therefrom into the micro-channels created in the skin.

Control unit 30, containing switching unit 50 and battery 52, is preferably designed for repeated use, to be removably attached to disposable skin patch 40. Before use, control unit 30 is fitted onto patch 40, and a protective tab (not shown) on the lower surface of patch 40 is preferably removed, exposing the one or more electrodes 60, and, in drug delivery systems, the active substance. One or more optional alignment pins 32 are preferably incorporated into control unit 30 and/or skin patch 40 to maintain proper alignment therebetween. Fitting control unit 30 to patch 40 also couples electrical contacts 62 on a lower surface of control unit 30 with electrical contacts 58 on an upper surface of skin patch 40. In some other preferred embodiments of the present invention (not shown), control unit 30 and skin patch 40 are constructed as one integrated unit.

Figure 1B:
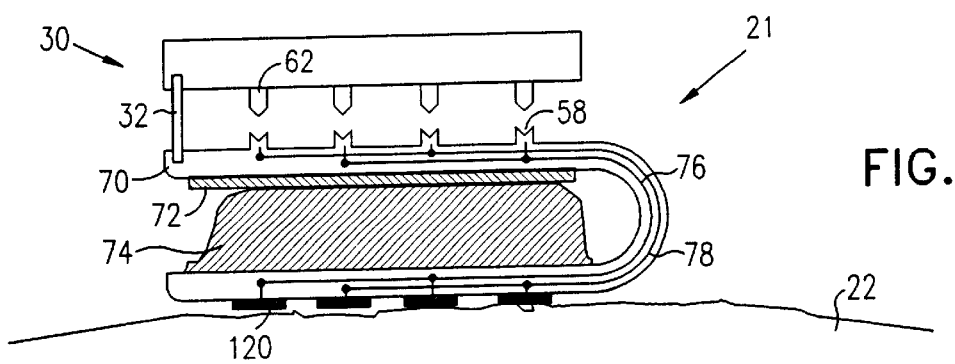
FIG. 1B is a schematic, partly sectional illustration of another device for transdermal transport of a substance, in accordance with a preferred embodiment of the present invention.

FIG. 1B is a schematic, partly sectional illustration of another device 21 for transdermal transport of a substance, in accordance with a preferred embodiment of the present invention. Device 21 operates in substantially the same manner as device 20, described hereinabove, but device 21 is preferably used in an add-on configuration with commercially available medical patches. Typically, a medical patch 74 is coupled to a porous, thin, flexible, and disposable electrode patch 70, which is used to create micro-channels in skin 22 so as to enable enhanced flow of an active substance stored within medical patch 74 through electrode patch 70 and into skin 22.

Electrode patch 70 is preferably constructed such that electrical contacts 58 thereof are coupled to electrical contacts 62 of control unit 30 and carry charge through flexible leads 76 and 78 internal to patch 70, in order to create an electric field between electrodes 120 placed against the surface of skin 22. Prior to use, medical patch 74 is placed onto electrode patch 70, typically on the opposite side of patch 70 from electrodes 120. An adhesive on the underside of medical patch 74 preferably secures the two patches together. Subsequently, electrode patch 70 is folded over, as shown in FIG. 1B, such that an upper surface of patch 74 is secured through an adhesive 72 to electrode patch 70. During operation of device 21, the active substance preferably diffuses from the lower surface of patch 74 into, and then through, patch 70 into skin 22. Device 21 is thus compatible with a broad range of currently available active or passive medical patches, which are typically of the same general construction (thin shell, internal reservoir of active substance, porous and adhesive-coated undersurface).

It is understood, of course, that device 21 as described is only one of many ways to implement some aspects of the present invention. Alternatively, for example, electrode patch 70 is not folded over; instead, control unit 30 is placed next to medical patch 74 on top of electrode patch 70. Further alternatively, control unit 30 has electrical contacts on its upper surface to which are coupled the electrical contacts of the electrical patch.

Figure 2:
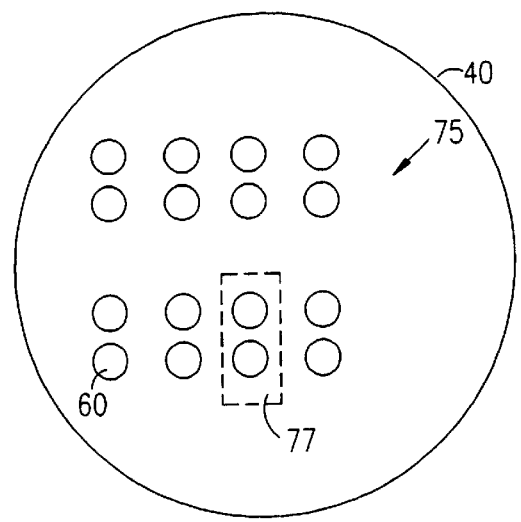
FIG. 2 is a schematic bottom view of the device of FIG. 1A, in accordance with a preferred embodiment of the present invention.

FIG. 2 is a schematic bottom view of skin patch 40 from FIG. 1A, showing array 75 of electrodes 60, in accordance with a preferred embodiment of the present invention. Although array 75 as shown comprises sixteen electrodes, it is understood that in some implementations the array might be smaller, while in others the array might be larger, for example 50×50 or even more, so as to enable a greater amount of the active substance to be delivered or analyte to be extracted. Electrodes 60 in this embodiment are preferably organized into eight electrode sets 77, such that most of the charge leaving one electrode in a set goes to the other electrode in that set, and generally does not go to electrodes in an adjacent set. Electrode sets 77 are further preferably densely packed in order to maximize the transdermal transfer rate. By way of illustration and not limitation, the density may range from 4–100 electrode sets/cm$^2$. Each electrode set typically generates at least one micro-channel before a threshold of current or total charge transfer is passed, responsive to which switching unit 50 preferably causes current to the electrode set to be terminated or reduced, as described herein.

Figure 3:
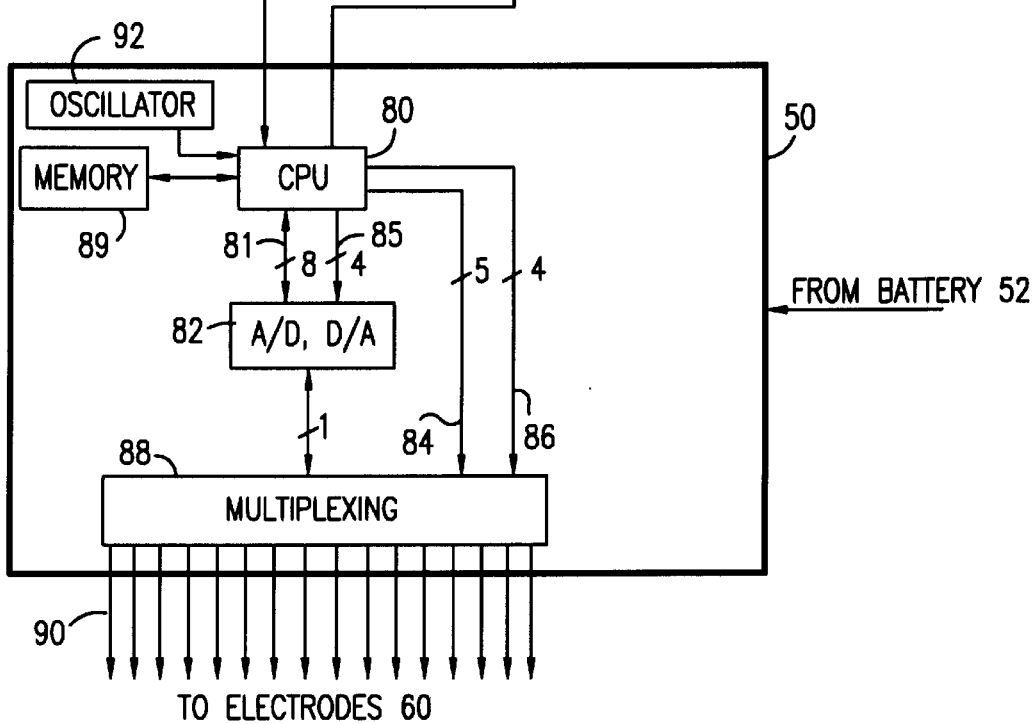
FIG. 3 is a schematic illustration of a switching unit in the device of FIG. 1A, in accordance with a preferred embodiment of the present invention.

FIG. 3 is a schematic illustration of switching unit 50 in device 20 of FIG. 1A, configured to control a 4×4 array of electrodes 60, as in FIG. 2, in accordance with a preferred embodiment of the present invention. Switching unit 50 preferably comprises a CPU 80 which actively controls the voltage V(t) applied to sixteen conductors 90 leading to electrodes 60. CPU 80 monitors the current flow, I(t), through each of conductors 90 leading to electrodes 60 in order to determine whether a characteristic of the current (e.g., time-integrated current, I, dI/dt, $d^2I/dt^2$) has surpassed a threshold, indicating micro-channel formation. The CPU terminates current flow to any electrode for which the threshold has been surpassed. Alternatively or additionally, in some applications, some of electrodes 60 are generally not used to initiate channel formation, but serve primarily to allow CPU 80 and/or other circuitry to monitor electrical properties of skin 22.

CPU 80, which receives a clock signal from an oscillator 92, preferably communicates with and controls electrodes 60 through eight data lines 81 and four control lines 85 which lead to an A/D-D/A converter 82, and by five address lines 84 and four control lines 86 which lead to a multiplexing unit 88. It will be understood by one skilled in the art that there are many methods to monitor and control current through a plurality of conductors, and that using a CPU, A/D-D/A converter and multiplexing unit as described herein is just one of these. Generally, data lines 81 carry in alternation a low byte and a high byte of data between the CPU and A/D-D/A converter 82. Typically, 10 bits of data, representing a desired voltage for one of the sixteen electrodes, are converted to an analog voltage in A/D-D/A converter 82, and this voltage is passed by multiplexing unit 88 to an appropriate electrode, the electrode selection being determined by the binary values represented in address lines 84. In many applications, fewer than 10 bits are required to define voltages for the respective electrodes, and circuitry within switching unit 50 is accordingly simpler.

Intermittently, CPU 80 enters a current-sensing mode, wherein switching unit 50 continues to drive current through conductors 90, but the CPU changes the state of control lines 85 and 86 in order to measure the current flow through conductors 90. Responsive to the change in control lines 86, multiplexing unit 88 measures a current through one of conductors 90, converts this measurement to a voltage, and passes the voltage to A/D-D/A converter 82 which in turn passes the digital value representing the current to the CPU. Preferably, CPU 80 scans through each of the sixteen electrodes, detects a present current flow value, stores this value in an optional memory unit 89, optionally compares the value with prior values for the same electrode in order to calculate $\int I(t)dt$, dI/dt and/or $d^2I/dt^2$, and regulates the potential of that electrode responsive to the current measurement and/or optional calculation. It will be understood by one skilled in the art that CPU 80, oscillator 92, and memory 89 could be replaced by other circuitry able to perform generally the same functions.

Figure 4:
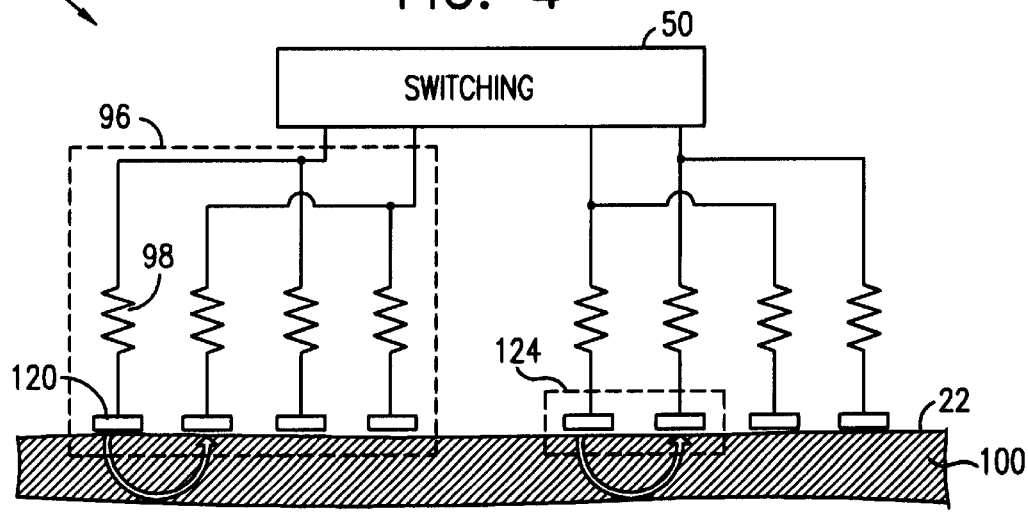
FIG. 4 is a schematic illustration of an electrode assembly, in accordance with a preferred embodiment of the present invention.

FIG. 4 is a schematic illustration of an electrode assembly 94, comprising a plurality of electrodes 120, which are placed on skin 22 in order to generate micro-channels in the stratum corneum 100, in accordance with a preferred embodiment of the present invention. Electrodes 120 in assembly 94 are grouped in sometimes overlapping sets of two or more electrodes, forming a plurality of electrode sets 124, one of which is indicated with a dashed line in FIG. 4. Current, coming from switching unit 50, generally flows from one electrode in each electrode set to the other electrodes of the set. An arrow going between the two electrodes in set 124 indicates the preferred flow of current.

Preferably, the spacing between electrodes in each electrode set is smaller than about 0.1 mm, although for some applications it may range from (by way of illustration and not limitation) 0.1 mm to about 0.3 mm. Generally, the distance is set such that an electric field penetration depth is achieved which is substantially of the same magnitude as the thickness of the stratum corneum, so that the current mostly does not enter epidermal tissue underlying the stratum corneum. Experimental results have shown that the depth of deepest ablation is generally similar to the electrode spacing, so maintaining the spacing between about 0.01 mm and about 0.1 mm optimizes generation of micro-channels while substantially reducing damage, sensation and/or pain in the innervated dermis and in the epidermal tissue below the stratum corneum.

At any point in the skin in a vicinity of two electrodes placed thereon, the electric field generated between the electrodes can be viewed as having fundamentally two components: a component perpendicular to the skin, which generally causes current flow perpendicular to the skin; and a lateral component, which generally causes current flow parallel to the skin. At a point in the skin infinitesimally below one of the electrodes, the perpendicular component is generally large and/or greater than the lateral component. The present invention seeks generally to maximize the ratio of the lateral component to the perpendicular component at the depth corresponding to the interface between the deepest portion of the stratum corneum and the most superficial portion of the remainder of the epidermis. An electric field at the base of the stratum corneum having a relatively large lateral component generates current flow predominantly in the stratum corneum, with relatively little current flow into the underlying epidermal tissue. Thus, using methods and apparatus of the present invention, tissue ablation occurs mostly in the stratum corneum, as desired, and largely does not occur in the underlying tissue.

In some applications of the embodiment shown in FIG. 4, it is preferred to print electrodes 120 directly on skin 22, typically (a) by stamping the electrodes thereon; (b) by employing a transfer patch of a conductive substance; and/or (c) by other techniques known in the art. Switching unit 50 preferably sends current to the printed electrodes via printed ports (not shown) on the upper surface of the electrodes. In uses of the present invention for transdermal drug delivery, the conductive substance preferably contains an active substance, typically dissolved or suspended therein. Alternatively or additionally, it is desirable for the printed electrode to disconnect from the switching unit or power source at substantially the same time as ablation of the stratum corneum is completed. This "self-quenching" feature of the printed electrodes is typically achieved by controlling fabrication of the electrodes, in particular by regulating the thickness and/or chemical composition thereof. Printed electrodes comprising a silver-based emulsion ink preferably undergo thermal fusion within the ink responsive to high current flow, resulting in a decrease in electrical conduction therethrough.

As discussed hereinabove with reference to FIG. 3, switching unit 50 monitors current flow to electrodes 60 (or electrodes 120, shown in FIG. 1B and subsequent figures), and selectively terminates the flow to one or more electrodes upon a determination that ablation of stratum corneum 100 has occurred. Making reference to FIG. 4, a cluster 96 of electrodes is a grouping of electrodes 120, which are typically in very close mutual proximity, and are therefore assumed to overlie an area of skin 22 which has generally uniform properties. By way of illustration and not limitation, cluster sizes generally range from about 4 mm² to about 100 mm². Switching unit 50 preferably monitors and terminates the current flow through the electrodes in cluster 96 collectively (i.e. for all of the electrodes, not individually for each electrode). Alternatively or additionally, current through electrodes 120 in cluster 96 is determined by monitoring the current in only a subset of the electrodes, and assuming the value derived therefrom to be generally representative of current through each of the other electrodes. Upon a determination by switching unit 50 that stratum corneum 100 under cluster 96 has been ablated, the current flow to all of the electrodes in cluster 96 is substantially terminated. Monitoring of clusters of electrodes generally simplifies control circuitry associated with the invention, while not substantially decreasing the performance thereof.

Optional resistive elements 98, coupled in series between switching unit 50 and electrodes 120, limit the power dissipation in the skin following the large increase of conductivity in the epidermis associated with ablation of the stratum corneum. Typical values for resistive elements 98 range from 1 kOhm–100 kOhms, but in some applications may have values outside of this range.

Figure 5:
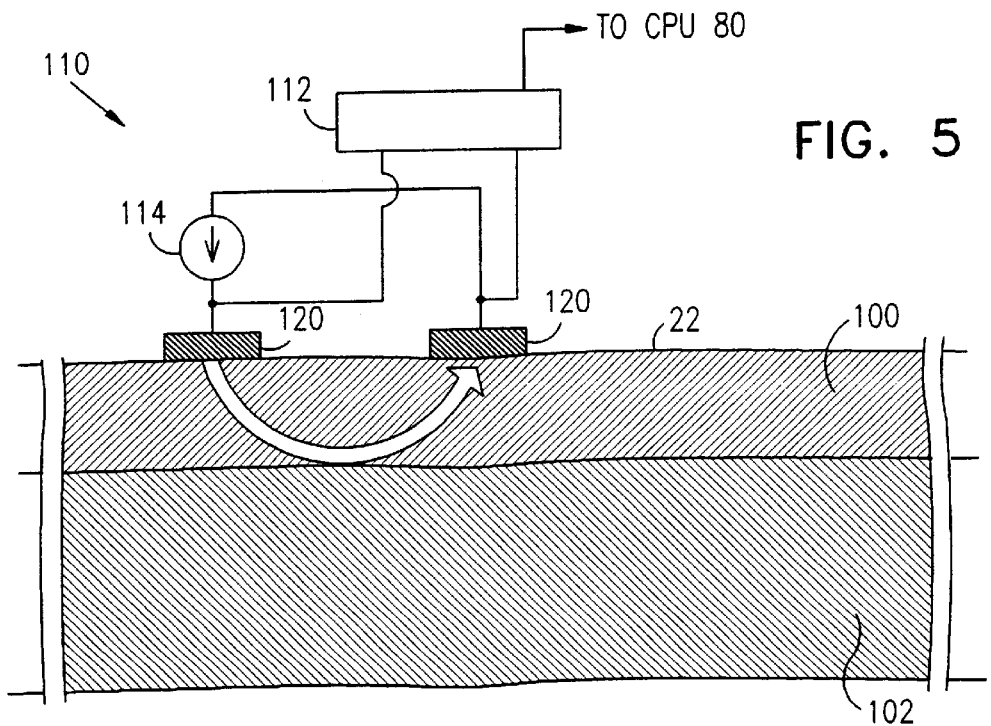
FIG. 5 is a schematic illustration of another electrode assembly, in accordance with a preferred embodiment of the present invention.

FIG. 5 is a schematic illustration of another electrode assembly 110, comprising a current source 114 coupled to drive charge through electrodes 120 on skin 22, in accordance with a preferred embodiment of the present invention. Current source 114 preferably comprises a source of electrical power (for example, a battery) connected in series with an inductive element which, due to pulse charging, exhibits properties of a current source, thereby limiting the power dissipated in underlying epidermal tissue 102 following the drop in resistance of the epidermis associated with substantially complete ablation of stratum corneum 100. Alternatively or additionally, current-limited source 114 comprises active components such as transistors, op-amps, commercially-available "ideal" current sources, etc., which maintain the current through the skin generally constant after ablation of the stratum corneum, so that the power dissipated ($P=I^2R$) will decrease with the reduced resistance of the skin upon the electrical breakdown of stratum corneum 100.

Prior to breakdown, the impedance between electrodes 120 is high, producing a generally large voltage drop therebetween, so the energy dissipated in the skin ($P=VI$) has a desired high value. The energy dissipation rate is preferably sufficient to cause electrical breakdown of stratum corneum 100 in a short time, which is typically less than 50 milliseconds, but may range from about 1 to about 1000 milliseconds. Reported values of the voltage needed to break down stratum corneum 100 spread over a range of approximately 5–1000 volts. For the purposes of the present invention, it has been found that an inter-electrode voltage of approximately 100 volts generally ablates stratum corneum 100 without causing significant damage to underlying tissue 102. It is understood, however, that for some applications or types of subjects/patients, lower or higher interelectrode voltages may be more suitable.

Intermittently or continuously during application of the electric field to skin 22, an optional voltage sensing unit 112 preferably measures the interelectrode voltage and sends a signal corresponding thereto to CPU 80 or other circuitry in switching unit 50, which regulates the current produced by source 114 responsive to the signal. Alternatively or additionally, voltage sensing unit 112 comprises a comparator which intermittently or continuously compares the interelectrode voltage to a pre-determined threshold value, and signals source 114 when the voltage is below the threshold. In either case, the CPU, circuitry and/or comparator preferably control source 114 to reduce or terminate current flow responsive to a drop of the interelectrode voltage below the threshold value.

Figure 6:
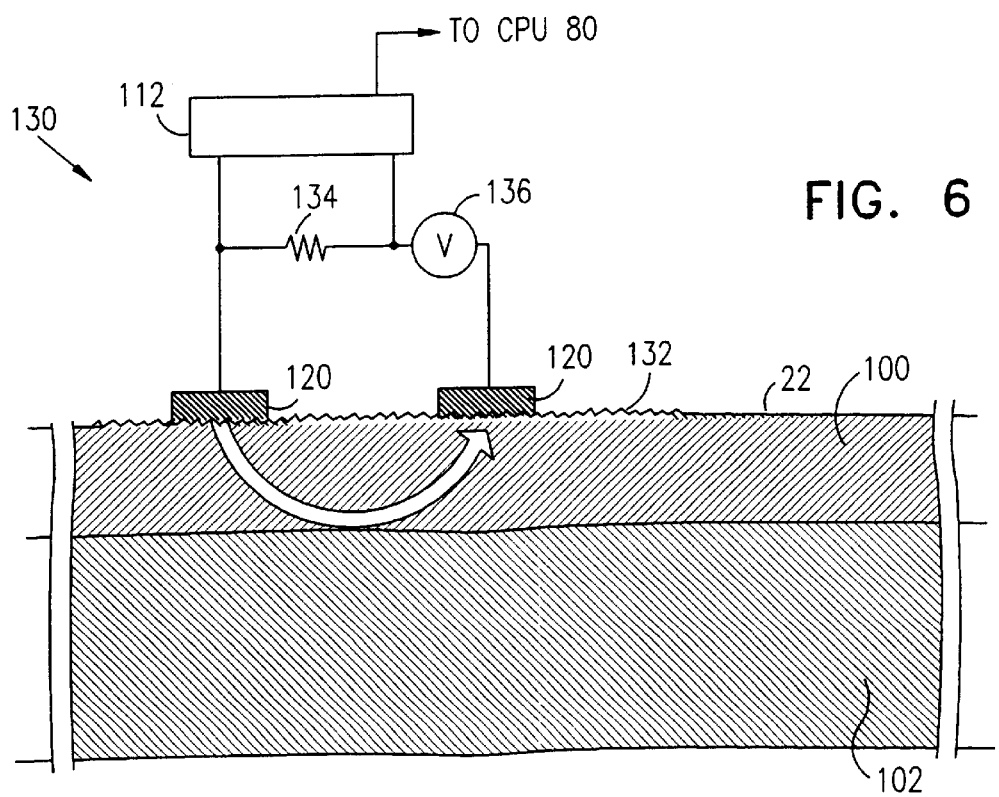
FIG. 6 is a schematic illustration of yet another electrode assembly, in accordance with a preferred embodiment of the present invention.

FIG. 6 is a schematic illustration of another electrode assembly 130, comprising a voltage source 136 coupled in series through an optional resistive element 134 to two electrodes 120 on the surface of skin 22, in accordance with a preferred embodiment of the present invention. Optional voltage sensing unit 112 measures the voltage drop across resistive element 134 in order to determine the current passing therethrough. In a manner substantially similar to that described hereinabove with reference to FIG. 5, unit 112 and/or CPU 80 and/or other circuitry in switching unit 50 regulate the output of voltage source 136 responsive to the measurement made by unit 112. Preferably, when the voltage drop across element 134 exceeds a predetermined threshold value, this is used as an indication of stratum corneum ablation and causes the voltage generated by source 136 to be reduced or terminated responsive thereto.

In applications of the embodiment shown in FIG. 6, if optional resistive element 134 and optional voltage sensing unit 112 are not used, it is preferable to employ other means for significantly reducing the current flow through electrodes 120 after micro-channel formation. This is preferably done by using "self-quenching" printed electrodes, as described hereinabove with reference to FIG. 4.

Alternatively or additionally, a conductivity-enhancing substance 132 is applied to skin 22 prior to placement of electrodes 120 thereon. Substance 132 typically improves current flow into skin 22 by decreasing the electrical resistance at the interface between electrodes 120 and skin 22. Experimental results indicate that use of substance 132 has the additional desired effect of increasing the above-mentioned ratio of the lateral component of the electric field to the perpendicular component thereof. In particular, it is believed that substance 132 diffuses into stratum corneum 100 and reduces the lateral resistance and lateral breakdown strength of the stratum corneum. By virtue of the relationship $P=V^2/R$, the increased conductivity in stratum corneum 100 (prior to the breakdown thereof) deriving from the presence of substance 132 produces a relatively high rate of energy dissipation in the stratum corneum. However, as ablation occurs, it has been observed that the enhanced conductivity path due to substance 132 is substantially removed, resulting in an increase in resistance and the desired attendant decrease in energy dissipation in the skin.

Substance 132 typically comprises a conductive cream, gel and/or ink. In some applications of this embodiment, substance 132 additionally comprises a material which has a high diffusion coefficient into the skin and promotes the increased lateral component of the electric field relative to the perpendicular component, as described hereinabove. Alternatively or additionally, "pre"-iontophoresis, using a relatively weak electric field, is used to enhance the flow of substance 132 into the outer layer of the skin before application of the stronger electric fields which create the micro-channels. The presence of the conductive substance in the skin subsequent to the pre-iontophoresis is believed to increase the rate of micro-channel creation. Pre-iontophoresis is typically implemented by applying, for example, a 3 volt DC field between the electrodes for 30 seconds in order to drive substance 132 into the skin. Alternatively or additionally, a larger AC current which produces micro-channels is supplemented by a simultaneous small DC current which supports iontophoresis of substance 132 and thereby enhances micro-channel creation.

In some applications, when micro-channels are created in order to enhance transdermal delivery of an active substance, the active substance is preferably incorporated in substance 132.

Figure 7:
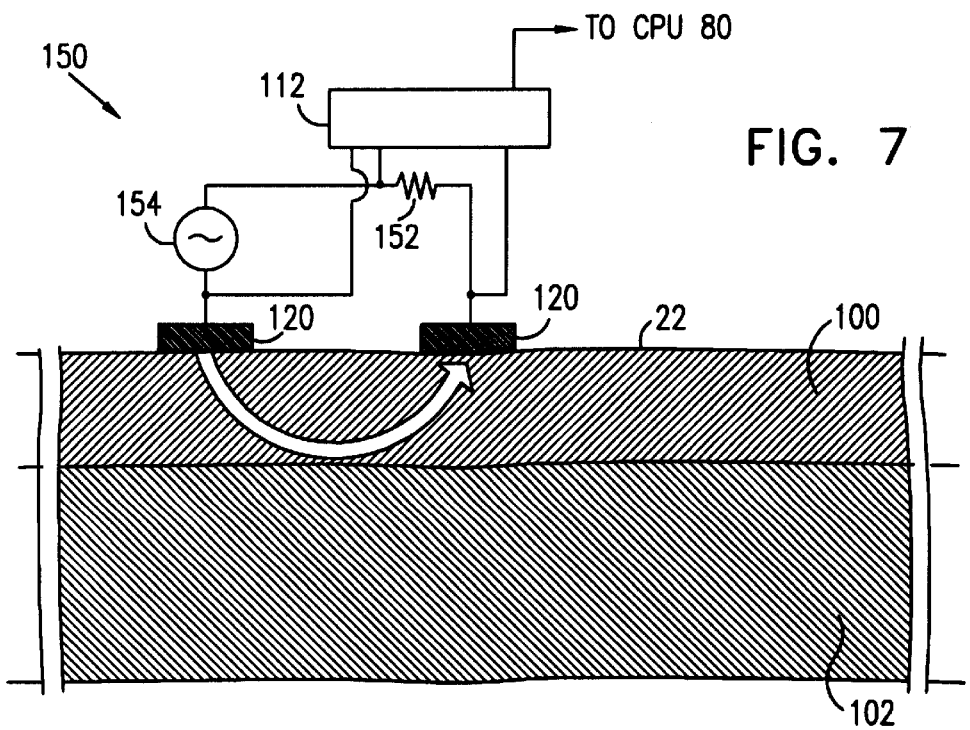
FIG. 7 is a schematic illustration of still another electrode assembly, in accordance with a preferred embodiment of the present invention.

FIG. 7 is a schematic illustration of another electrode assembly 150, comprising an AC current source 154 coupled in series with an optional resistive element 152 in order to drive current through electrodes 120 and skin 22, in accordance with a preferred embodiment of the present invention. It has been reported that the driving frequency of current through skin has a significant effect on the sensation or pain experienced by a subject. See, for example, *Principles of Applied Biomedical Instrumentation*, by L. Geddes and L. Baker, John Wiley & Sons, 1989, which is incorporated herein by reference. For the purposes of the present invention, a 10 kHz driving frequency has been found to yield good results, although any frequency between about 100 Hz and about 10 MHz is appropriate for most applications. Depending on properties of a subject's skin, it is sometimes appropriate to use driving frequencies outside of this range. Optionally, the driving frequency is cyclically modulated between two endpoints (e.g., 2 kHz and 15 kHz) during application of the electric field, such that a graph representing frequency versus time (not shown) is typically sinusoidal or triangular in character.

Stratum corneum 100 generally displays properties of a simple insulator when exposed to DC current, but displays significant capacitance under AC stimulation, particularly when the driving frequency is above 1 kHz. At these frequencies, current flow through the stratum corneum dissipates energy therein, contributing to the heating and ultimate ablation of the stratum corneum. The pre-ablation capacitance produces a measurable phase shift between the voltage across the electrodes and the current flowing therebetween, which phase shift is seen to be significantly reduced upon commencement and completion of the ablation of the stratum corneum. Sensing unit 112 is typically used to detect this phase shift by measuring the inter-electrode voltage, as described hereinabove, and by determining the current flow through electrodes 120, preferably by measuring the voltage drop across optional resistive element 152. The change of the phase shift from baseline is preferably used by sensing unit 112 and/or CPU 80 and/or other circuitry in switching unit 50 to indicate breakdown of the stratum corneum, responsive to which current flow to electrodes 120 demonstrating such a change preferably is reduced or terminated.

As described hereinabove, in some applications, substance 132 is applied to skin 22, and a DC current is superimposed on the AC current in order to cause iontophoresis of substance 132 during micro-channel creation.

Alternatively or additionally, in applications using AC and/or DC current delivery (as in FIGS. 5, 6 and 7), the duration of charge delivery is limited by means of an optional ordinary timer circuit (not shown). Further alternatively or additionally, the total charge delivered (or root mean squared charge in AC operation modes) is limited using methods known in the art. For example, energy storage components such as capacitors and/or inductors can be used to modulate charge delivery.

Although in the embodiments shown in FIGS. 5, 6, and 7, passing a threshold of current or voltage is used as an indicator of when to reduce the current applied to the skin, other functions of the current and/or voltage, such as derivatives, time-integrals, and/or powers thereof may also be evaluated in order to determine when the current should be reduced.

Figure 8A:
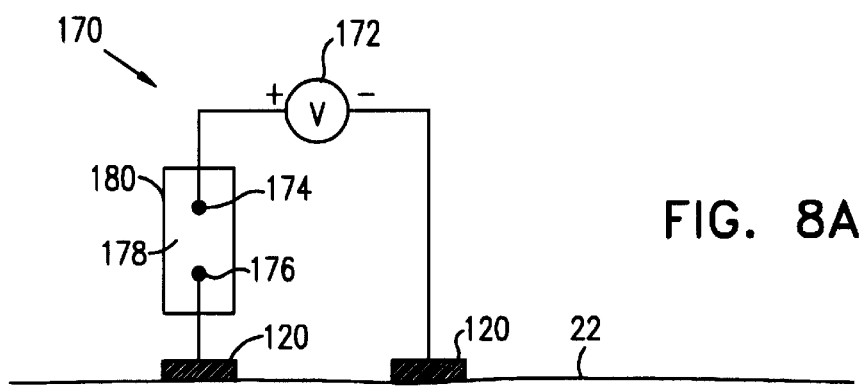
FIGS. 8A and 8B are schematic illustrations of charge-limited electrode assemblies, in accordance with preferred embodiments of the present invention.

FIG. 8A is a schematic illustration of a charge-limited electrode assembly 170, comprising an electrolyte cell 180 connected in series between a power source 172 and electrodes 120, in accordance with a preferred embodiment of the present invention. Electrolyte cell 180 comprises an anode 174 and a cathode 176, both immersed in an electrolyte solution 178, which acts as a medium for current flow from anode 174 to cathode 176. As current flows through cell 180, cathode 176 is steadily consumed by electrolysis until electrolyte cell 180 becomes substantially non-conductive. In this manner, consumption of cathode 176 progresses at a rate which is generally proportional to the current flowing therethrough. By modifying the initial mass of cathode 176, cell 180 can be built to allow a flow of charge that substantially does not exceed a predetermined value.

Figure 8B:
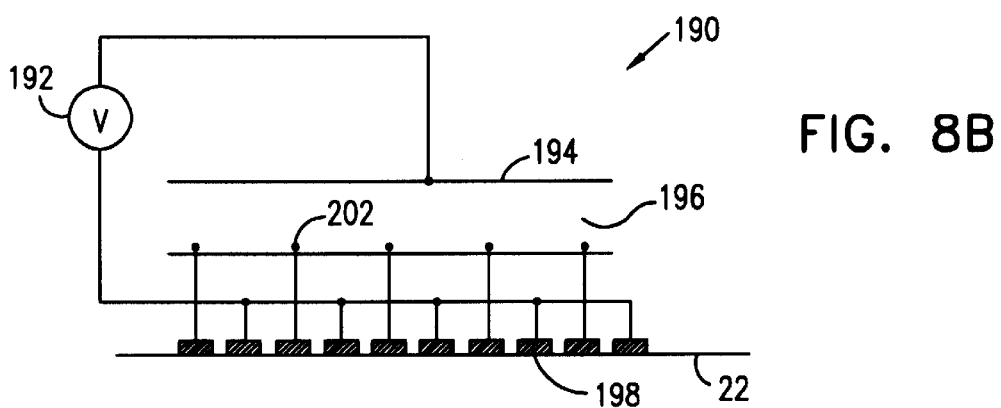

FIG. 8B is a schematic illustration of another charge-limited electrode assembly 190, comprising a power source 192 which sends current to a large-area anode 194 from which it flows through an electrolyte solution 196 to multiple cathodes 202, in accordance with a preferred embodiment of the present invention. In general, the charge-limiting functions embodied in assembly 190 are similar to those described with respect to the embodiment shown in FIG. 8A. Anode 194 comprises a fibrous material, such as paper, having fibers aligned in a generally vertical direction, perpendicular to the surface of skin 22. Alternatively or additionally, anode 194 is in very close proximity to cathodes 202, typically from about 0.1 mm to about 2 mm, in order to enhance independent termination of current through electrodes 198 coupled to cathodes 202, by reducing lateral conduction within the electrolyte solution.

Figure 9:
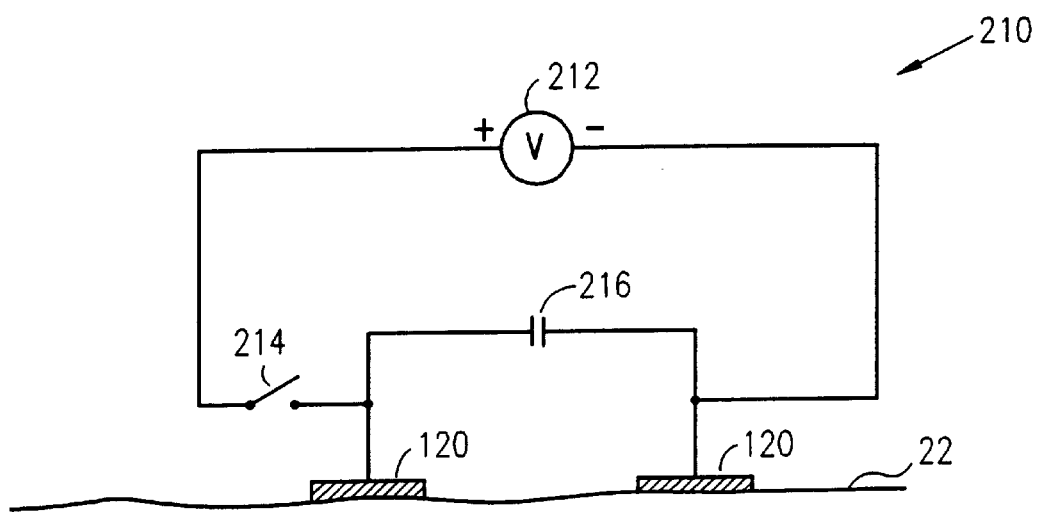
FIG. 9 is a schematic illustration of another charge-limited electrode assembly, in accordance with a preferred embodiment of the present invention.

FIG. 9 is a schematic illustration of yet another charge-limited electrode assembly 210, comprising a power source 212 in series with a controlled switch 214, in accordance with a preferred embodiment of the present invention. Source 212 and switch 214 are connected in series with a capacitor 216 across electrodes 120, which are applied to skin 22. Capacitor 216 is preferably utilized in order to limit the total charge delivered through electrodes 120 to generally not more than the charge-holding capacity of capacitor 216 at a designated voltage generated by source 212, given by the formula q=CV, wherein C is the capacitance of the capacitor. By way of illustration and not limitation, for an applied voltage of 50 volts, a capacitor whose capacitance ranges from about 1 nF to about 0.2 $\mu$F is appropriate.

A typical operational sequence in this preferred embodiment comprises: (a) turning on source 212; (b) closing switch 214, which results in substantially all of the current from source 212 going through and charging low-impedance capacitor 216; (c) opening switch 214 and turning off source 212; (d) allowing the discharge from capacitor 216 to drive the ablation of the stratum corneum; and (e) passively terminating the process responsive to complete discharge of capacitor 216.

Figure 10:
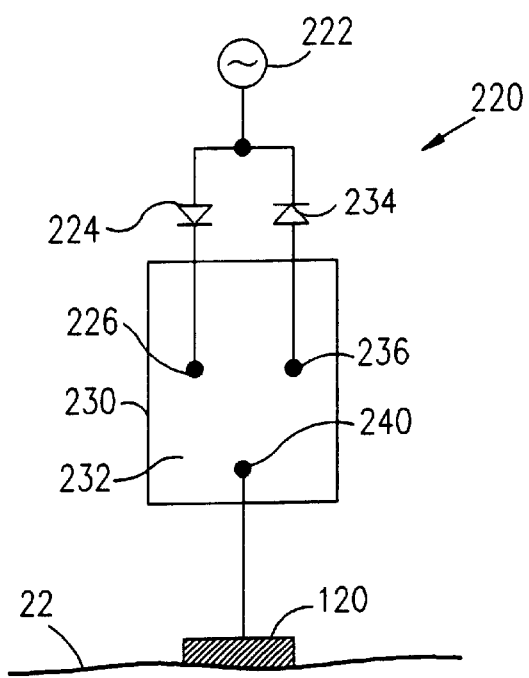
FIG. 10 is a schematic illustration of yet another charge-limited electrode assembly, in accordance with a preferred embodiment of the present invention.

FIG. 10 is a schematic illustration of still another charge-limited electrode assembly 220, comprising an AC source 222 coupled in series to an electrolyte cell 230, electrode 120, and skin 22, in accordance with a preferred embodiment of the present invention. Cell 230 preferably comprises two alternating nodes 226 and 236 and a common node 240, all nodes being immersed in an electrolyte solution 232. Except as will be described below, the function of electrolyte cell 230 is substantially similar to that of electrolytic charge-limiting devices described hereinabove with reference to FIGS. 8A and 8B.

AC source 222 produces a voltage difference across electrodes 120 (only one electrode is shown), which cycles between positive and negative phases at a predetermined frequency, in order to provide the energy to ablate stratum corneum 100 in skin 22. During the positive phase, a diode 224 in electrolyte cell 230 passes current to cause alternating node 226 to act as an anode and common node 240 to act as a cathode, which is subsequently consumed by the electrolysis thereof during each positive phase. Conversely, during the negative phase, diode 224 blocks conduction through alternating node 226, halting the consumption of common node 240 associated with the positive phase. In a similar manner, during the negative phase, a second diode 234 passes current which allows alternating node 236 to act as a cathode (which is consumed) and common node 240 to act as an anode. When a sufficient quantity of charge has passed through electrolyte cell 230, common node 240 is completely consumed, and cell 230 becomes substantially non-conductive. Preferably, the properties of electrolyte cell 230 are determined so that the cell becomes non-conductive after passing a quantity of charge which correlates with breakdown of the stratum corneum.

Figure 11A:
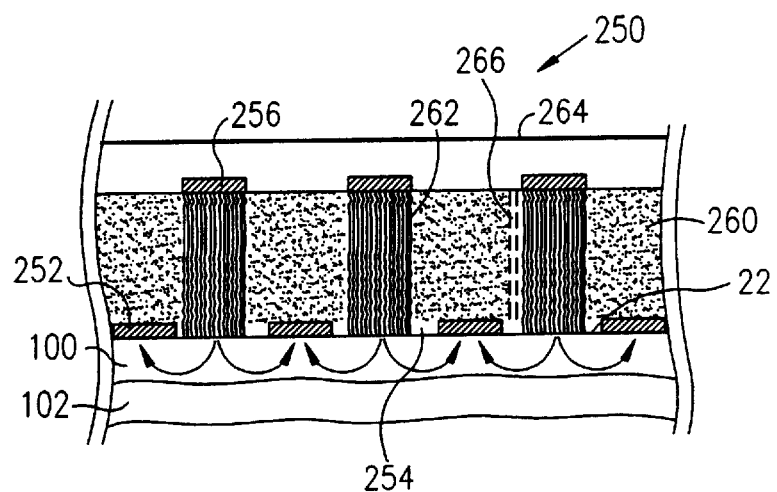
FIG. 11A is a schematic side view of a concentric electrode assembly, in accordance with a preferred embodiment of the present invention.
Figure 11B:
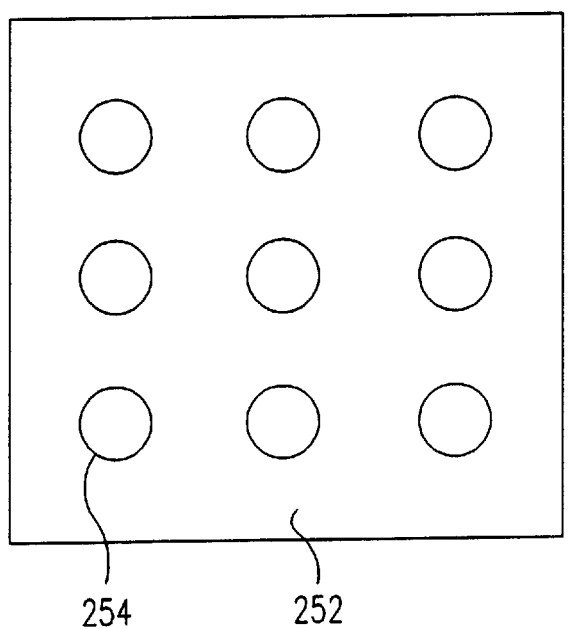
FIG. 11B is a schematic top view of a common electrode layer in the concentric electrode assembly of FIG. 11A, in accordance with a preferred embodiment of the present invention.

Reference is now made to FIGS. 11A and 11B which are, respectively, a schematic side view of a concentric electrode assembly 250 and a schematic top view of a common electrode layer 252 in assembly 250, in accordance with a preferred embodiment of the present invention. A substantially non-conductive substrate 260 overlies common electrode layer 252. Perforations 254 in layer 252 allow passage therethrough of electrodes 262, which receive charge through optional resistive members 256 from a charging bus 264 overlying substrate 260. Electrodes 262, which preferably comprise a plurality of conductive fibers, are electrically coupled to skin 22, and cause charge to pass into skin 22 and subsequently out of skin 22 through common electrode layer 252, in order to ablate stratum corneum 100.

In some preferred applications, one or more pores 266 traversing substrate 260 allow flow of active substances/analytes through substrate 260 from/to a reservoir (not shown) above substrate 260. It is noted that fabrication of concentric electrode assembly 250 is substantially similar to the process of flexible printed circuit production, which is well known in the art.

It will be appreciated generally that the preferred embodiments described above are cited by way of example, and the full scope of the invention is limited only by the claims.

What is claimed is:

1. A method for ablating stratum corneum epidermidis of a subject, comprising:

applying electrical energy between points on the skin, so as to cause ablation of an area of the stratum corneum during a first time period; and applying a drug to the ablated area during a second time period, subsequent to the first time period, so that passage of the drug through the stratum corneum is facilitated by the ablation.

2. A method according to claim 1, wherein applying the electrical energy comprises applying the energy for less than about 1 second.

3. A method according to claim 2, wherein applying the electrical energy comprises applying the energy for less than about 200 milliseconds.

4. A method for ablating stratum corneum epidermidis of a subject, comprising:

applying electrical energy between points on the skin, so as to cause ablation of an area of the stratum corneum during a first time period; and extracting an analyte through the ablated area during a second time period, subsequent to the first time period, so that passage of the analyte through the stratum corneum is facilitated by the ablation.

5. A method according to claim 4, wherein applying the electrical energy comprises applying the energy for less than about 1 second.

6. A method according to claim 5, wherein applying the electrical energy comprises applying the energy for less than about 200 milliseconds.

7. A method for passing electrical current through the skin of a subject, comprising:

placing a plurality of electrodes against the skin at respective points;

applying the current through the electrodes; and coupling to at least one of the electrodes an electrically conductive dissolving element, the element being characterized by having a dissolving rate generally proportional to the current passing therethrough, and by becoming substantially nonconductive responsive to a function of the current passing therethrough.

8. A method for ablating stratum corneum epidermidis of skin of a subject, comprising applying electrical energy to the skin of the subject between points on the skin which are spaced less than about 0.3 mm apart, so as to cause ablation of the stratum corneum.

9. A method according to claim 8, wherein applying the energy between the two points comprises applying the energy between points on the skin which are spaced about 001–0.1 mm apart.

10. A method for ablating the stratum corneum epidermidis of a subject, comprising:

placing a plurality of electrodes against the subject's skin at respective points; and applying electrical energy to the plurality of the electrodes so as to induce an electrical current to flow through the stratum corneum, causing ablation of narrow channels through the stratum corneum at the respective points.

11. A method according to claim 10, wherein placing the plurality of the electrodes comprises placing at least one set of two or more electrodes against the skin, and wherein applying the electrical energy comprises inducing the current to flow between the electrodes in the at least one set.

12. A method according to claim 10, wherein placing the plurality of the electrodes comprises placing a common electrode and a plurality of individual electrodes against the skin, and wherein applying the electrical energy comprises inducing the current to flow between the plurality of individual electrodes and the common electrode.

13. A method according to claim 10, wherein applying the energy comprises ablating the area of the stratum corneum in order to allow a substance to pass through the area.

14. A method according to claim 13, wherein placing the plurality of electrodes comprises placing an array of the electrodes against the skin, wherein a density of the electrodes in the array is determined responsive to a desired transdermal transfer rate of the substance.

15. A method according to claim 13, and comprising delivering a drug through the area.

16. A method according to claim 13, and comprising extracting an analyte through the area.

17. A method according to claim 10, wherein skin layers beneath the stratum corneum are substantially not ablated.

18. A method according to claim 10, wherein applying the electrical energy comprises puncturing the skin.

19. A method according to claim 10, wherein applying electrical energy comprises:

causing a current to flow through the points on the skin; and substantially reducing the current flow through the skin responsive to variation of a characteristic of the current.

20. A method according to claim 19, wherein the characteristic is drawn from a list consisting of: a magnitude of the current; a time-integration of the current; a first time-derivative of the current; and a second time-derivative of the current.

21. A method according to claim 19, wherein causing the current to flow comprises passing current to the one or more points on the skin through one or more respective limited-conduction units, wherein the units allow current below a threshold value to flow therethrough substantially unimpeded, and wherein the units become substantially nonconductive if the current flowing therethrough exceeds a limited-conduction threshold value.

22. A method according to claim 19, wherein causing the current to flow comprises passing current to the one or more points on the skin through one or more respective electrically conductive dissolving elements, each element characterized by a dissolving rate generally proportional to the current passing therethrough, and becoming substantially nonconductive when the total charge having passed therethrough exceeds a dissolving element threshold value.

23. A method according to claim 19, wherein reducing the current flow comprises reducing the current at one of the respective points substantially independently of the current at another one of the respective points.

24. A method according to claim 19, wherein reducing current flow comprises:

monitoring the current flow through one of the plurality of electrodes; and reducing the current flow through another one of the plurality of electrodes responsive thereto.

25. A method according to claim 10, wherein applying electrical energy comprises generating alternating current, a frequency thereof being above about 100 Hz.

26. A method according to claim 25, wherein the frequency is between about 1 kHz and about 300 kHz.

27. A method according to claim 10, wherein applying electrical energy comprises generating alternating current and modulating a frequency thereof between a first frequency value and a second frequency value.

28. A method according to claim 10, wherein placing the plurality of electrodes comprises placing two of the plurality of electrodes at a separation therebetween that is less than about 0.3 mm.

29. A method according to claim 28, wherein placing the plurality of electrodes comprises placing the two of the plurality of electrodes at a separation between about 0.01 mm and about 0.1 mm.

30. A method according to claim 10, wherein placing the plurality of electrodes comprises:

applying a conduction-enhancing material to an area on the surface of the subject's skin in order to enhance current flow through the skin; and placing the electrodes on the material,
wherein the electrical resistance of the conduction-enhancing material increases responsive to a function of the current flow therethrough.

31. A method according to claim 10, wherein placing the plurality of electrodes comprises:

placing on the skin a common electrode which has a plurality of perforations therethrough; and placing on the skin a plurality of positive electrodes, each positive electrode passing through a respective perforation in the common electrode,
such that current from the power source flows from each positive electrode through the skin to the common electrode.

32. A method according to claim 10, and comprising positioning in a vicinity of the electrodes a medical patch containing the substance, such that ablation of the stratum corneum increases a transport rate of the substance from the patch into the skin.

* * * * *